United States Patent [19]
Allison et al.

[11] Patent Number: 5,569,649
[45] Date of Patent: Oct. 29, 1996

[54] ANTI-INFLAMMATORY TREATMENT METHOD

[75] Inventors: Anthony C. Allison, Belmont, Calif.; Carl F. de Vos Albrecht, Durbanville, South Africa; Petrus B. Kruger, Cape Town, South Africa; Marthinus J. van der Merwe, Bellville, South Africa

[73] Assignee: Phytopharm (NA) N.V., Netherlands Antilles

[21] Appl. No.: 259,961

[22] Filed: Jun. 14, 1994

[51] Int. Cl.⁶ .......................... A61K 31/70; C07H 15/00
[52] U.S. Cl. .................... 514/25; 514/886; 536/4.1
[58] Field of Search ................ 514/25, 886; 536/4.1

[56] References Cited

U.S. PATENT DOCUMENTS

| | | | |
|---|---|---|---|
| 4,160,860 | 7/1979 | Pegel | 536/5 |
| 4,198,401 | 4/1980 | Pegel | 424/195.1 |
| 4,644,085 | 2/1987 | Drewes et al. | 568/729 |
| 4,652,636 | 3/1987 | Drewes et al. | 536/4.1 |
| 4,956,502 | 9/1990 | Wenteler et al. | 568/729 |

FOREIGN PATENT DOCUMENTS

| | | |
|---|---|---|
| 0092226 | 10/1983 | European Pat. Off. |
| 0206765 | 12/1986 | European Pat. Off. |
| 0587396 | 3/1994 | European Pat. Off. |
| 1259503 | 4/1969 | United Kingdom |
| 1417272 | 3/1973 | United Kingdom |
| 2120650 | 12/1983 | United Kingdom |

OTHER PUBLICATIONS

Galeffi et al., *Planta Medica*, vol. 55, pp. 318–320, (1989).
M. Nicoletti, et al., "Hypoxidaceae. Medicinal uses and the norlignan constituents", *J. of Ethnopharmacology*, 36:95–101 (1992).
Albrecht, C. F., et al., "Hypoxoside as a possible non-toxic, prodrug for the chemoprophylaxis of colon cancer in man", from *Cancer Society of New Zealand Colorectal Cancer Conference Handbook*(Auckland, New Zealand, Feb. 15–19, 1993).
Di Giannuario, A., et al., "The Analgesic Property of Hypoxoside, a Glucoside from *Hypoxis obtusa*", *Pharmacological Research*27(1): 95–96 (1993).
Friend, D. R., and G. W. Chang, "A Colon–Specific Drug–Delivery System Based on Drug Glycosides and the Glycosidases of Colonic Bacteria", *J. Med. Chem.*27: 261–266 (1984).
van der Merwe, M., et al., "Interaction of the Di–Catechols Rooperol and Nordihydroguaiaretic Acid with Oxidative Systems in the Human Blood. A Structure–Activity Relationship", *Biochemical Pharmacology*45(2): 303–311 (1993).

*Primary Examiner*—John Kight
*Assistant Examiner*—Howard C. Lee
*Attorney, Agent, or Firm*—Vincent M. Powers; Susan T. Evans

[57] ABSTRACT

A method of treating inflammation in a subject by administering a therapeutically effective amount of a compound having the structure:

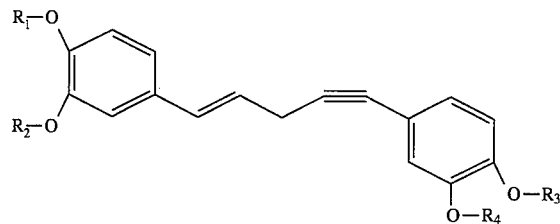

where $R_1$ to $R_4$ are the same or different and are each selected from the group consisting of H, an alkylacyl group, an arylacyl group, or a C-1-linked saccharide.

13 Claims, 4 Drawing Sheets

ANTI-INFLAMMATORY TREATMENT METHOD

1. FIELD OF THE INVENTION

The present invention relates to methods of treating inflammatory conditions.

2. REFERENCES

Friend, D. R., et al., *J. Med. Chem.* 27:261–266 (1984).
Kruger, et al., *J. Chrom.* 612:191–198 (1993).

3. BACKGROUND OF THE INVENTION

Inflammatory conditions are a significant cause of disabilities that accompany a variety of disease states. Drugs currently in use for treating inflammatory conditions include anti-inflammatory agents such as corticosteroids, and non-steroidal anti-inflammatory drugs; immunosuppressive agents such as methotrexate, azathioprine, cyclosporin A, and cyclophosamide; and anti-rheumatic agents such as gold salts, sulfasalazine, antimalarials, and penicillamine. However, many of these compounds have undesirable side effects or are limited in therapeutic efficacy. Prolonged administration of glucocorticoids, for example, can often produce adverse systemic effects, e.g., on carbohydrate and calcium metabolism.

In the more recent past, there has been growing evidence that the cytokines TNF-α and IL-1β are important mediators of inflammation and septic shock. Accordingly, identification of small molecule drugs capable of inhibiting the production of both of these cytokines would be useful for the development of novel anti-inflammatory treatment methods.

4. SUMMARY OF THE INVENTION

The present invention is based on the applicants' discovery that the compound known as rooperol has significant anti-inflammatory activity whereas O-glycosylated conjugates of rooperol do not.

In one aspect, the present invention relates to a method of treating an inflammatory disease in a mammalian subject. In the method, a therapeutically effective amount of a compound is administered to a subject in need of such treatment, wherein the compound has the structure (Formula I):

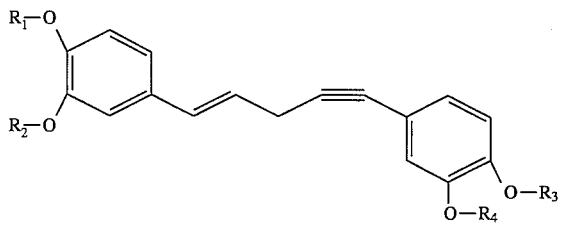

where $R_1$ to $R_4$ are independently selected from the group consisting of H, a lower alkylacyl group, an arylacyl group, a lower arylalkylacyl group, or a C-1-linked saccharide.

In one embodiment, the method is useful for treating inflammation of the large intestine. In one preferred embodiment, $R_1$ and $R_3$ are glucose, and $R_2$ and $R_4$ are H, and the compound is administered orally. The method is particularly useful for treating ulcerative colitis and diverticulitis. In a particular embodiment, for treating ulcerative colitis, at least one of $R_1$ and $R_2$ and at least one of $R_3$ and $R_4$ are independently glucose or a lower alkylacyl group, and the compound is administered rectally.

In another embodiment, for treating Crohn's disease in the small intestine, at least one of $R_1$ and $R_2$ and at least one of $R_3$ and $R_4$ are lower alkylacyl groups, and the compound is administered orally. In one preferred embodiment, $R_1$ through $R_4$ are acetyl groups.

The method of the invention is also useful for treating respiratory inflammation, wherein a compound in accordance with the invention is administered by inhalation.

In another embodiment, for use in treating an inflammatory condition associated with the skin, the compound is administered topically.

In yet another embodiment, the method of the invention can be used in the treatment of eye inflammation, where the compound is applied to the subject's eye(s).

The method of the invention may also be used in treating septic shock, for which the compound is preferably administered intravenously.

In another embodiment, for treating inflammation or fibrogenesis in the peritoneal, pelvic, or pleural cavity, the compound may be administered by injection into the affected cavity.

In another aspect, the invention includes a method of reducing reperfusion injury in a mammalian subject, by administering to the subject a therapeutically effective amount of a compound in accordance with the formula shown above.

These and other objects and features of the invention will become more fully apparent when the following detailed description of the invention is read in conjunction with the accompanying drawings.

DETAILED DESCRIPTION OF THE INVENTION

I. Definitions

Figure 1:
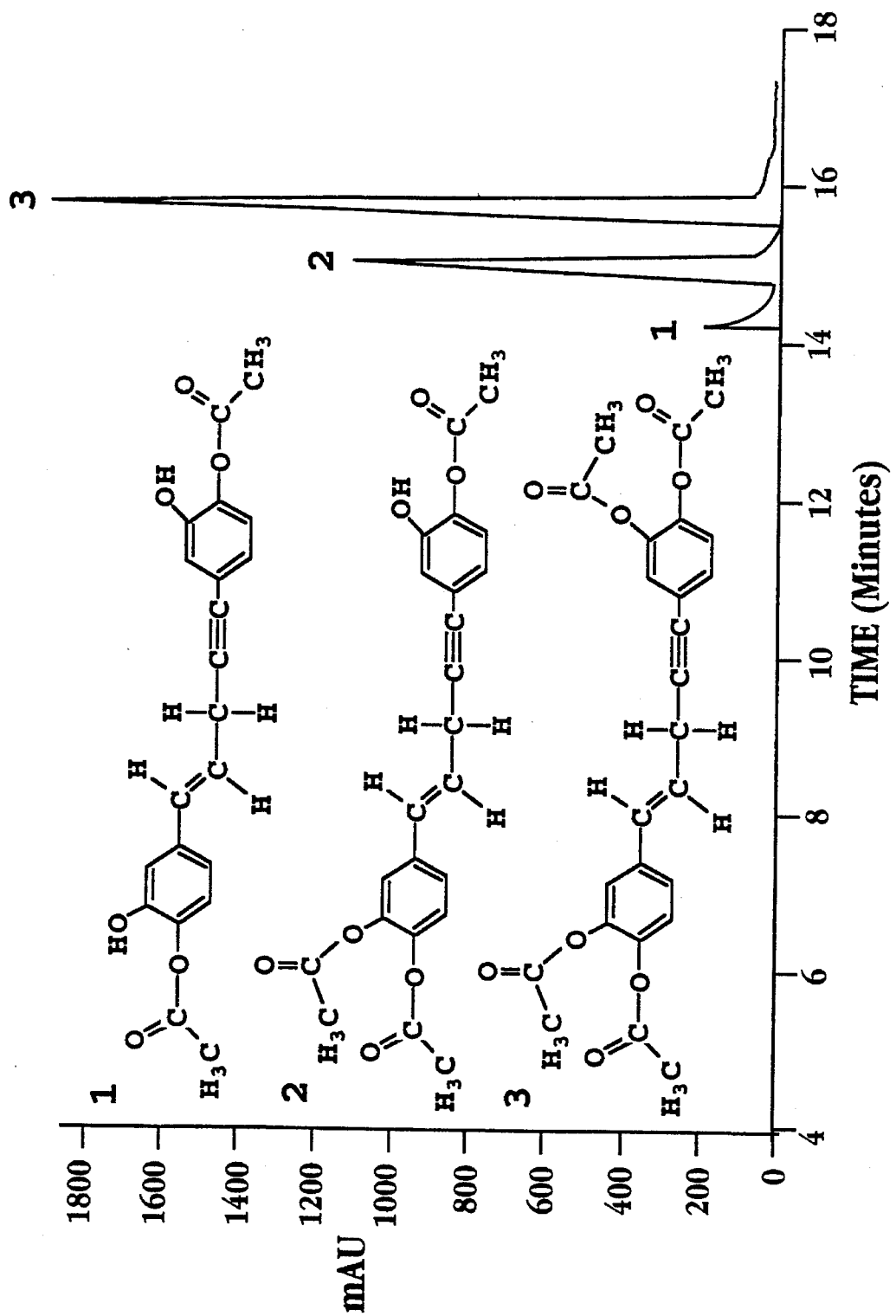
FIG. 1 shows an HPLC chromatogram of a mixture of acetylated rooperol compounds obtained by the procedure described in Example 3.

The terms below as used herein have the following meanings unless indicated otherwise.

"Hypoxoside" refers to the compound having the structure shown at Formula I above, where $R_1$ and $R_3$ are glucose groups joined to the 4-oxygen atoms in each catechol ring by a β-glycosyl linkage, and $R_2$ and $R_4$ are H.

"Rooperol" refers to the compound having the structure shown at Formula I, where $R_1$ to $R_4$ are all H.

Compounds having the structure shown at formula I, where at least one of the $R_n$ groups is not hydrogen, may also be referred to herein as rooperol esters or rooperol glycosides, as appropriate.

A compound that is "substantially pure" refers to a compound having a purity of greater than 95% on a weight basis with respect to impurities stemming from synthesis of the compound or isolation of the compound from a natural (e.g., plant) source.

"Method of Treating Inflammation" encompasses treatment of a disease in a mammalian subject, and particularly in a human subject, and includes (i) prophylactic treatment to prevent the onset of the disease, (ii) arresting the development of clinical symptoms of the disease, and/or (iii) bringing about a regression in the clinical symptoms of the disease.

"Acyl" refers to a radical having the form —C(O)R, where R is an alkyl, aryl, or an arylalkyl group.

"Alkyl" refers to a fully saturated monovalent radical containing only carbon and hydrogen, and which may be cyclic, branched or a straight chain. Examples of alkyl groups are methyl, ethyl, n-butyl, n-heptyl, isopropyl, 2-methylpropyl, cyclopropyl, cyclopropylmethyl, cyclobutyl, cyclopentyl, cyclopentylethyl, and cyclohexyl.

"Lower alkyl" refers to an alkyl radical of one to six carbon atoms, as exemplified by methyl, ethyl, n-butyl, i-butyl, t-butyl, isoamyl, n-pentyl, and isopentyl.

"Alkylacyl" and "lower alkylacyl" refer to radicals having the form —C(O)R, where R is an alkyl or lower alkyl group, respectively.

"Aryl" refers to a substituted or unsubstituted monovalent aromatic radical having a single ring (e.g., benzene) or two condensed rings (e.g., naphthyl). Other examples include heterocyclic aromatic ring groups having one or more nitrogen, oxygen, or sulfur atoms in the ring, such as furyl, pyrrole, pyridyl, and indole.

"Arylacyl" refers to a radical having the form —C(O)R, where R is an aryl group.

"Arylalkylacyl" refers to a radical having the form —C(O)R, where R is an arylalkyl group, i.e., an aryl group linked to a carbonyl carbon by an intervening alkyl group, e.g., phenylmethyl, or phenylpropyl. A "lower arylalkylacyl group" refers to an arylalkylacyl group in which the intervening alkyl group contains one to six carbon atoms.

II. Preparation of Compounds

In one aspect, the invention includes an anti-inflammatory preparation comprising a substantially pure compound having the structure shown at Formula I above. This section describes methods of preparing such compounds.

A. Hypoxoside Preparation

The diglucoside, hypoxoside, can be obtained from plants of the Hypoxidaceae family by methods well known in the art (e.g., U.S. Pat. No. 4,652,636, which is incorporated herein by reference). This compound is useful as a pro-drug for anti-inflammatory use and may also serve as a convenient starting material for preparing rooperol and rooperol derivatives.

Hypoxoside is isolable in particular from species in the Hypoxis genus, such as *Hypoxis acuminata, Hypoxis nitida, H. obtusa-nitada, H. laifolia, H. rigiduli*, and *H. rooperi;* and from other plant sources such as *Spiloxene schelechteri*.

In brief, corms from a selected plant source are shredded and dried in a convection oven. The dried material is milled to fine particles, and the resulting powder is extracted by stirring the powder in methanol or ethanol for half an hour to a day or more. The resultant extract typically contains 50–55% by weight of hypoxoside.

Further purification can be achieved by reversed phase high performance liquid chromatography (HPLC), which typically affords hypoxoside in greater than 95% purity by weight. Details of such purification can be found in Example 1.

B. Rooperol and Derivatives

Rooperol may be obtained by treating hypoxoside with a β-glucosidase to remove the attached glucose groups, as illustrated in Example 2. In brief, the hypoxoside is incubated with almond β-glucosidase (10:1 ratio (w:w) of hypoxoside:glucosidase) at pH 5.5 for several hours at 37° C. The rooperol product is collected by ether extraction and dried. It is preferable that rooperol be kept in an oxygen-free environment since rooperol is susceptible to air oxidation.

The isolated rooperol compound is a convenient starting material for preparing ester derivatives for use as pro-drugs in accordance with the invention.

Rooperol esters in which one or more of the $R_n$ groups are acyl groups can be prepared from rooperol by standard acylation/esterification methods. In one approach, esterification is accomplished by reaction of rooperol with the desired acylating agent in the form of an acid anhydride, in the presence of a weak base such as pyridine. The reaction is continued until the maximum amount of the desired ester product has formed. The desired ester product can be purified from the reaction mixture by standard methods, e.g., HPLC.

Example 3 describes the formation of di-, tri-, and tetraacetyl esters of rooperol obtained by reaction of 1 equivalent of rooperol with 3 equivalents of acetic anhydride. An HPLC chromatogram of the crude reaction mixture is shown in FIG. 1. As can be seen, the tetraester was the predominant product, although a significant amount of triester was also present, with a minor amount of diester. The distribution of products can be altered by suitable adjustment of the duration of the reaction as well as the relative amounts and proportions of the reactants.

Under the above reaction conditions, the para-hydroxyl (4-hydroxyl) groups in the rooperol starting material are more reactive than the meta-hydroxyl (3-hydroxyl) groups by virtue of greater stability of the phenolic anionic forms of the former. This difference in reactivity can be exploited to preferentially form a diester in which only the para-hydroxyl groups are acylated.

Alternatively, reacting rooperol with an excess amount of anhydride for sufficient time can afford the tetraester product exclusively. In this case, purification of the desired product is simplified by the absence of the other possible ester products so that preparative silica gel chromatography (as opposed to HPLC) generally suffices for final purification of the ester product.

In a second general approach, esterification can be carried out by reacting rooperol with an excess amount of a carboxylic acid. A catalytic amount of a strong acid, such as sulfuric acid, may be included to hasten the esterification process. The reaction is continued until the maximum amount of the desired ester product has formed. The product can be purified from the reaction mixture by standard methods as above.

In a third approach, rooperol esters can be formed by reaction of rooperol with a carboxylic acid chloride or bromide as acylating agent. Typically, a hindered base such as triethylamine or 2,6-dimethylpyridine is included to scavenge the HCl generated in the reaction. After completion of the reaction, the reaction mixture is extracted to remove HCl salts, and the ester products are purified as above.

Rooperol and esters thereof may also be synthesized using the procedures described in U.S. Pat. Nos. 4,644,085 and 4,956,502, which are incorporated herein by reference.

With regard to rooperol glycoside compounds, while the hypoxoside is a preferred glycoside, other glycoside derivatives of rooperol may be used in accordance with the invention. Such rooperol glycosides may be prepared by conjugating rooperol with other reducing sugars such as ribose, arabinose, xylose, mannose, and galactose, through the C-1 carbon of the sugars.

Glycoside formation may be effected chemically, e.g., by reacting rooperol with a protected sugar compound in which C-1 has been activated by halogenation for coupling with the rooperol hydroxyl groups, and the sugar hydroxyls have been blocked by protecting groups (e.g., Friend et al., 1984). Alternatively, glycoside formation may be effected enzymatically using an appropriate glycosyltransferase.

C. Compound Formulations

Administration of the compounds of the invention in pure form or in an appropriate pharmaceutical composition, can be carried out via any of the accepted modes of administration of agents for similar utilities. Thus, administration can be, for example, oral, nasal, parenteral or topical. The formulations may take the form of solid, semi-solid, lyophilized powder, or liquid dosage forms, such as, for example, tablets, pills, capsules, powders, solutions, suspensions, emulsions, suppositories, retention enemas, creams, ointments, lotions, or aerosols, preferably in unit dosage forms suitable for simple administration of precise dosages.

The compositions typically include a conventional pharmaceutical carrier or excipient and may additionally include other medicinal agents, carriers, and adjuvants. Exemplary formulations are shown in Examples 10 and 11.

Preferably, the composition will be about 5% to 75% by weight of a compound or compounds of the invention, with the remainder consisting of suitable pharmaceutical excipients. For oral administration, such excipients include pharmaceutical grades of mannitol, lactose, starch, magnesium stearate, sodium saccharine, talcum, cellulose, glucose, gelatin, sucrose, and magnesium carbonate, for example. The composition may take the form of a solution, suspension, tablet, pill, capsule, powder, or sustained-release formulation, for example.

Preferably the compositions will take the form of a pill, tablet or capsule, and thus the composition will contain, along with the active ingredient, a diluent such as lactose, sucrose, or dicalcium phosphate, a disintegrant such as starch or derivatives thereof; a lubricant such as magnesium stearate; and a binder such a starch, gum acacia, polyvinylpyrrolidone, gelatin, cellulose and derivatives thereof.

The active compounds of the formulas may be formulated into a suppository comprising, for example, about 0.5% to about 50% of a compound of the invention, disposed in a polyethylene glycol (PEG) carrier (e.g., PEG 1000 [96%] and PEG 4000 [4%]).

Liquid compositions can be prepared by dissolving or dispersing compound (about 0.5% to about 20%), and optional pharmaceutical adjuvants in a carrier, such as, for example, aqueous saline, aqueous dextrose, glycerol, or ethanol, to form a solution or suspension. The active compounds may be formulated into a retention enema.

If desired, the composition to be administered may also contain minor amounts of non-toxic auxiliary substances such as wetting or emulsifying agents, pH buffering agents, such as, for example, sodium acetate, sorbitan monolaurate, or triethanolamine oleate.

Methods for preparing such dosage forms are known or will be apparent to those skilled in the art; for example, see *Remington's Pharmaceutical Sciences* (1980). The composition to be administered will, in any event, contain a quantity of the pro-drug and/or active compound(s) in a pharmaceutically effective amount for relief of the condition being treated when administered in accordance with the teachings of this invention.

Generally, the compounds of the invention are administered in a therapeutically effective amount, i.e., a dosage sufficient to effect treatment, which will vary depending on the individual and condition being treated. Typically, a therapeutically effective daily dose is from 0.1 to 100 mg/kg of body weight per day of drug. Most conditions respond to administration of a total dosage of between about 1 and about 30 mg/kg of body weight per day, or between about 70 mg and 2100 mg per day for a 70 kg person.

III. Biological Activity

This section describes studies which demonstrate the compound known as rooperol possesses anti-inflammatory activity. The studies also show that rooperol that reaches the bloodstream, e.g., following oral administration of hypoxoside, is converted to non-toxic conjugates which are cleared by the kidneys.

A. Suppression of Production of TNF-$\alpha$ and IL-1$\beta$

According to an important aspect of the invention, it has been discovered that rooperol has the ability to suppress the production of TNF-$\alpha$ and IL-1$\beta$ by lipopolysaccharide-stimulated human peripheral blood mononuclear cells (PBMCs).

In the study detailed in Example 4, cultured PBMCs enriched in monocytes were stimulated with lipopolysaccharide (20 µg/ml) in the presence and absence of rooperol at concentrations of 1–10 µM. After overnight incubation, the cells were collected and lysed, and the concentrations of TNF-$\alpha$ and IL-1$\beta$ were measured by ELISA. The results are shown in FIGS. 2A and 2B.

Figure 2A:
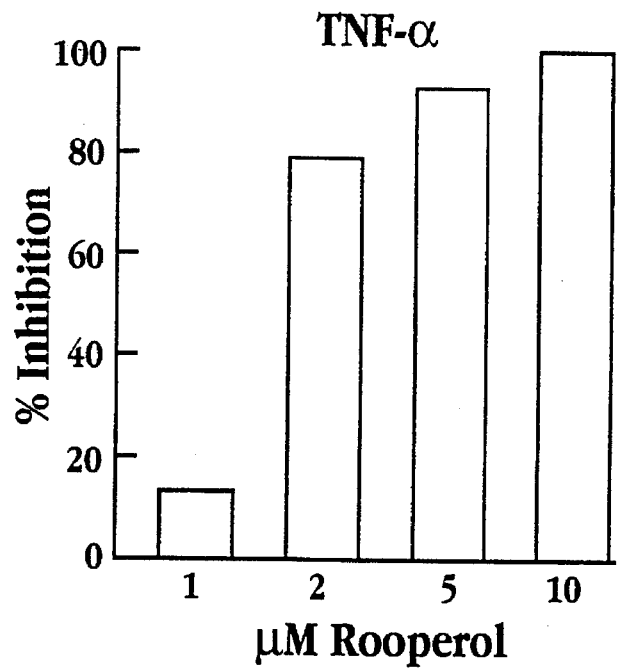
FIGS. 2A and 2B show dose-dependent inhibition, by rooperol, of the production of TNF-α and IL-1B by activated human mononuclear cells.
Figure 2B:
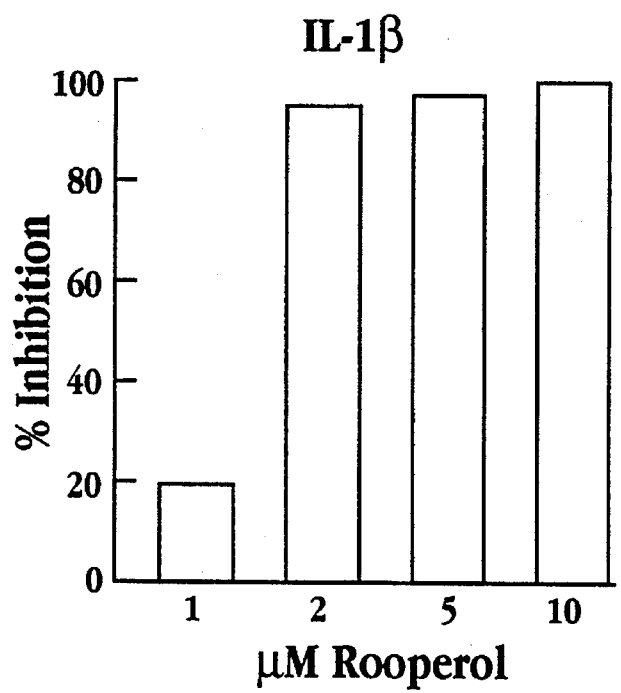

As can be seen from FIG. 2A, rooperol showed dose-dependent inhibition of TNF-$\alpha$ production, with nearly complete inhibition at a rooperol concentration of 10 µM, and half-maximal inhibition at a concentration between 1 and 2 µM. The results for IL-1$\beta$ (FIG. 2B) were similar, with half-maximal inhibition occurring again at a rooperol concentration between 1 and 2 µM.

These results show that rooperol is a potent inhibitor of the production of TNF-$\alpha$ and IL-1$\beta$, both of which are significant mediators of inflammation and septic shock. In contrast, hypoxoside (the 4,4-diglucuronide of rooperol) was inactive in the above assays.

B. Bioavailability of Rooperol in Humans

According to another important aspect of the invention, it has been found that the diglycoside, hypoxoside, when administered orally, is taken up rapidly into the bloodstream and is metabolized to non-toxic derivatives. These features are useful in controlling the level of drug in the serum, allowing rapid alleviation of any overdose by halting administration and allowing phase II metabolism to clear excess drug.

The administered compound may be rooperol or derivatives thereof. However, because rooperol is susceptible to air oxidation, it is preferable that the compound is an acetylated or glycosylated rooperol derivative, since acetylation or glycosylation is effective to substantially eliminate air-sensitivity, while at the same time providing a pro-drug which can be converted to rooperol in vivo.

Where such pro-drugs of the invention are administered orally to treat inflammation in the intestinal tract, the effects of the drug can be localized to either the small or large intestine by suitable choice of R groups, as discussed in section IV below. Rooperol generated in the intestinal tract and subsequently taken up in the bloodstream is inactivated by phase II metabolic processes, limiting the potential systemic effects of the rooperol.

Alternatively, where the compound is to be administered intravenously, for treating septic shock or reducing reperfusion injury for example, the effects of metabolism are offset by the fact that the compound is being introduced directly into the bloodstream, allowing sufficient drug to reach the site of interest before substantial inactivation of the drug has occurred.

Figure 3:
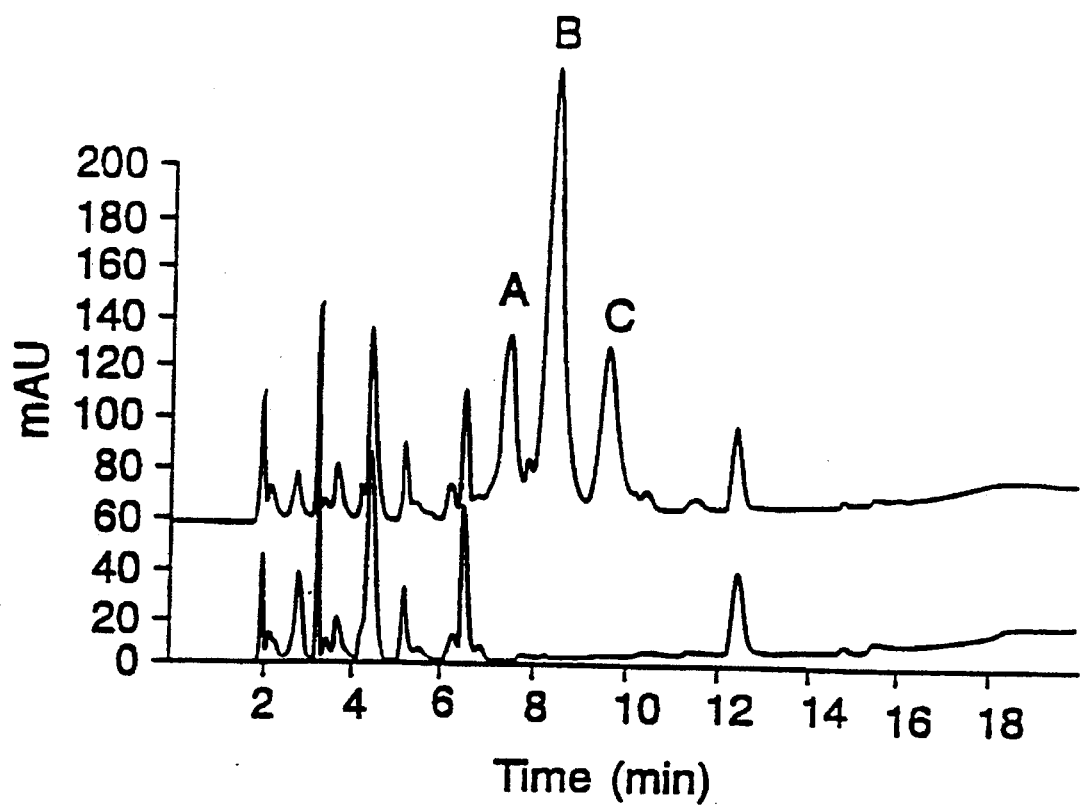
FIG. 3 shows HPLC chromatograms of blood samples obtained before (lower trace) and after (upper trace) oral administration of hypoxoside by a human subject; Peaks A, B, and C correspond to metabolites of rooperol.

Example 6 describes a study characterizing the metabolites that appear in the bloodstream following oral administration of hypoxoside. In brief, 1 g of hypoxoside was administered to a human subject, and two hours later, a blood sample was collected for analysis by the HPLC protocol from Example 5. Chromatograms of the subject's blood before and after drug administration are shown in FIG. 3.

As can be seen from the figure, the chromatograms of the two samples were identical but for the appearance of three new peaks designated A, B, and C (retention times of 7.6, 8.4, and 9.6 minutes, respectively). None of these peaks corresponded to rooperol or hypoxoside, based on the fact that the retention times of the latter two compounds under the same conditions are 12.2 minutes and 8.2 minutes, respectively.

Example 7 describes the characterization of the rooperol metabolites which were excreted in the urine of the same subject. Urine from the same volunteer as above was collected over 24 hours following administration of the hypoxoside. The collected sample was filtered and purified by passage through a column bed of C18-bonded silica.

Figure 4:
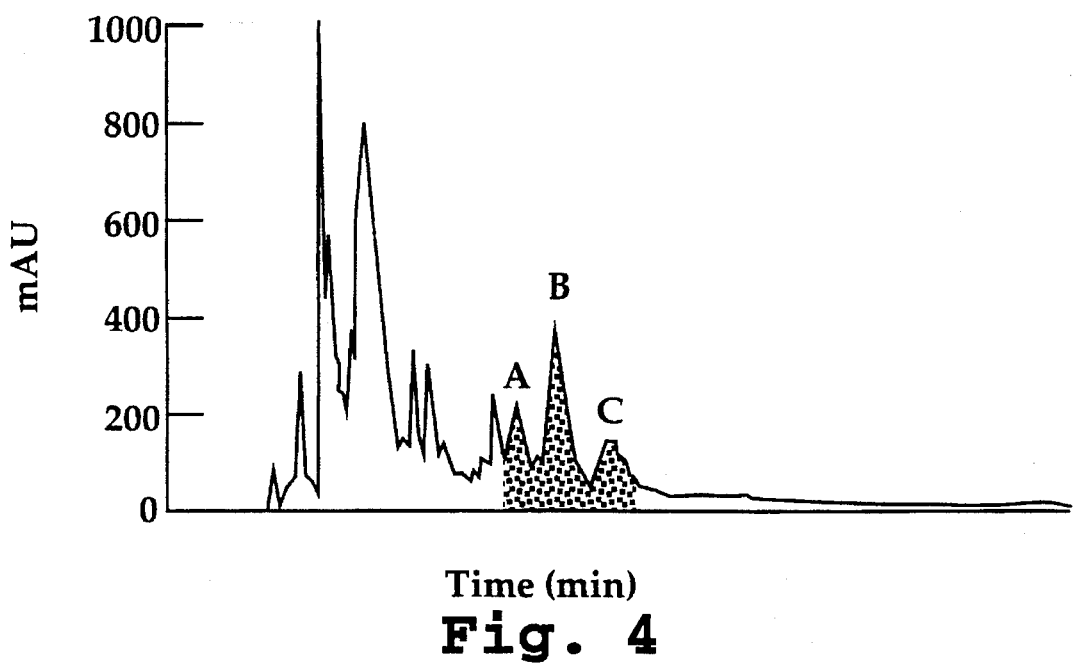
FIG. 4 shows an HPLC chromatogram of a urine sample obtained from the same human subject as FIG. 3.

FIG. 4 shows an HPLC chromatogram of the column-purified material. As can be seen, three peaks having the same retention times as peaks A, B and C found in serum were found in the urine sample. None of the other urinary peaks corresponded to rooperol or hypoxoside.

The three peaks were separately collected and further characterized by reaction with β-glucuronidase and/or arylsulfatase, as detailed in Example 8. The results showed that peak A corresponds to the 4,4'-diglucuronide of rooperol, peak B corresponds to a mixed glucuronide/sulfate rooperol derivative, and peak B corresponds to the 4,4'-disulfate derivative.

Figure 5:
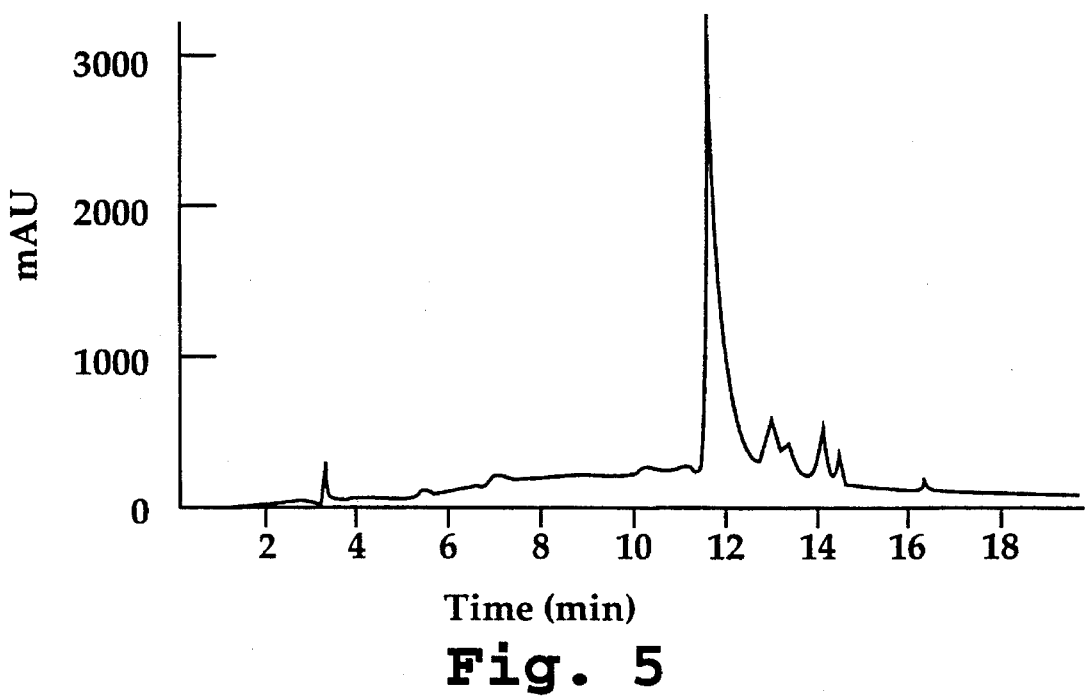
FIG. 5 shows an HPLC chromatogram of material extracted from a fecal specimen obtained from the same human subject as FIG. 3.

In addition, a fecal specimen was also obtained from the subject and, following extraction, was analyzed by HPLC as above (FIG. 5). Only one major peak was observed, with a retention time corresponding to that of rooperol. No peaks were detectable for hypoxoside, its mono-glucoside, or any other rooperol derivatives.

The exclusive presence of rooperol in the fecal specimen indicates that following oral administration of hypoxoside, rooperol is the chemical species available for absorption by the intestinal tract, and hence is the precursor of the observed serum metabolites.

IV. Treatment Method

The compounds of the invention are effective in methods of treating a variety of inflammatory conditions including inflammation of the large bowel, inflammation of the small intestine, inflammatory skin conditions, eye inflammation, septic shock, respiratory inflammation, and in reducing reperfusion injury following thrombosis or surgery. The compounds may be administered alone or concurrently with other therapeutic compounds appropriate for the given conditions being treated.

As noted in section IIIB. above, the administered compound can be rooperol (Formula I, $R_1$ to $R_4$=H), or more preferably, for use as a pro-drug, is an acylated or glycosylated derivative thereof. Rooperol itself possesses significant anti-inflammatory activity whereas glycosylated derivatives do not. Delivery of an acylated or glycosylated rooperol as a pro-drug to a site capable of removing the acyl or glycosylated groups is thus effective to produce rooperol at that site.

Whether acyl groups or glycosyl groups are used in the pro-drug depends on the nature of the inflammatory condition being treated. In either case, it is preferable that at least one of $R_1$ and $R_2$ and at least one of $R_3$ and $R_4$ in the pro-drug are non-hydrogen moieties, so that the pro-drug does not contain a benzene 3,4-diol moiety.

For treating inflammation of the large bowel by oral administration of drug, and in particular, for treating ulcerative colitis or diverticulitis, the administered compound is a polyglycoside such as hypoxoside. By virtue of its glycosyl groups, the rooperol glycoside compound when administered orally is not absorbed during passage through the small intestine. However, the glycoside is hydrolyzed by bacterial glycosidases in the large intestine, producing rooperol. Absorption of the rooperol by the intestinal mucosa is effective to reduce inflammation of the intestinal lining. Alternatively, where the compound is to be administered rectally, e.g., in the form of a suppository or enema, the compound may be either a glycosylated derivative or an acylated derivative, since both glycosidases and esterases are present to hydrolyze either of the pro-drug forms.

It will be appreciated that the compound of the invention may be administered concurrently with other suitable medications, such as antibacterial or antiulcer agents, to facilitate reduction of the inflammation.

For treating non-intestinal conditions, the compound is generally rooperol or an acylated rooperol, but not a rooperol glycoside. In a particularly preferred embodiment, where an acylated rooperol compound is used, the compound is preferably a tetraacyl compound, such as rooperol tetraacetate ($R_1$ through $R_4$=C(O)CH$_3$).

For treating inflammation in the small intestine, and particularly for treatment of Crohn's disease, the compound is administered orally, and at least one of $R_1$ and $R_2$ and at least one of $R_3$ and $R_4$ is an acyl group. These compounds, when administered orally, are absorbed in the small intestine and are hydrolyzed to rooperol by esterases located in the intestinal lining.

The method of the invention is also useful for treating inflammation associated with the skin, where preferably, at least one of $R_1$ and $R_2$ and at least one of $R_3$ and $R_4$ is an acyl group. Conditions for which the method can be used include psoriasis, actinic keratosis, acne vulgaris, and atopic dermatitis. The compound may be administered as a cream or lotion, for example, allowing the compound to pass into the skin. One formulation which has been found useful for treating inflammation of the skin is shown in Example 11. Esterases in the skin tissues are effective to hydrolytically remove the acyl group to produce rooperol at the site of inflammation.

The compounds used in the treatment of the skin can also be used in the treatment of eye inflammation. The compounds may be formulated, for example, as eyedrops, a cream, or a slow-release composition which is effective to release drug from a drug depot.

The method of the invention also finds use in treating respiratory inflammation. In particular, the method is useful for reducing the inflammation that accompanies asthma and chronic bronchitis. The compound is preferably of the same type as used for treating inflammation associated with skin tissue, and is preferably formulated as an inhalant.

The compound of the invention is also useful for treating septic shock. The compound is preferably of the same type as used for treating inflammation associated with skin, and is administered intravenously. Administration should be concomitant with fluid replacement and other measures to reverse or arrest hypotension.

More generally, for intravenous or oral administration, an acylated compound of the invention may include one or more morpholino substituents, e.g., $R_n$=morpholinoethylacyl, to improve serum lifetime of the compound (e.g., Lee et al., *Pharm. Res.* 7:61 (1990)).

For treating inflammation or fibrogenesis in the peritoneal, pelvic or pleural cavity, the compound is administered by injection. For this use, the compound is typically formulated as a lipid emulsion, a liquid suspension, or a slow-release composition.

In another aspect, the invention includes a method of treating reperfusion injury following thrombosis. The compounds are generally of the same type useful for treating skin. In the case of coronary thrombosis, the compounds are administered intravenously, for example, to reduce the damage that can occur at sites of occlusion once reperfusion has begun. Alternatively, for reperfusion following cerebral thrombosis, the compound may be administered intravenously or by injection into the cerebrospinal fluid. The method also finds use following surgical procedures that may have resulted in hypoxic tissue conditions or the creation of thrombi. The compound is preferably administered intravenously or topically.

The following examples illustrate but are not intended in way to limit the invention.

EXAMPLE 1

Preparation of Hypoxoside

In a general procedure, washed corms from *Hypoxis rooperi* are shredded, placed on drying trays, and dehydrated in a convection oven at 90° C. for 4.5 hours. The dried shreds are then milled to a particle size of 200 mesh, affording a brown powder. 12.5 kg of corms provide approximately 5.0 kg of dried powder. The milled powder (5.0 kg) is extracted with methanol (25 l) with stirring for 30 minutes at room temperature. Filtration of the slurry and vacuum evaporation provides 1.25 kg of light brown Hypoxis corm extract typically containing 50–55% by weight of hypoxoside.

Further purification of the hypoxoside extract was conducted by preparative HPLC as follows. A Shimadzu chromatography system was used (Kyoto, Japan), with the following components: an SCL-8A system controller, 2 LC-8A mobile phase delivery pumps, an SPD-6AV UV-Vis spectrophotometric detector, an FCV-130 AL reservoir inlet controller, and a FCV-100B fraction collector. The preparative column (50×300 mm) was packed with C8-bonded silica (Partisil Bioprep 20 µm C8 75A) from Whatman (Fairfield, N.J.).

Operating conditions involved isocratic delivery of mobile phase consisting of 15% acetonitrile in water (v/v) at a flow rate of 100 ml/minute. UV absorbance was monitored at 260 nm, and fractions of 250 ml were collected. Sample loading was conducted by dissolving dried hypoxoside extract (5 g) in 50 ml water and loading the resultant solution directly onto the column pre-equilibrated in water. Hypoxoside, dehydroxy-hypoxoside, and bis-dehydroxyhypoxoside eluted in sequence starting at a retention volume of 8.5 liters.

Fractions containing mono-components were selected on the basis of analytical HPLC analysis (Example 5), diluted with 3 parts water, and concentrated on C18-bonded silica (40 µm, preparative grade). Elution with methanol and subsequent evaporation of solvent yielded pure hypoxosides.

EXAMPLE 2

Preparation of Rooperol

Hypoxoside from Example 1 was incubated with µ-glucosidase from almonds (Sigma Chemical Co., St. Louis, Mo.) to liberate rooperol. Hypoxoside (100 mg) was dissolved in 0.1M acetate buffer (10 ml, pH 5.5) and β-glucosidase (10 mg) was added. The mixture was incubated for 4 hours at 37° C., following which the hydrolysis products were extracted with diethylether (1×5 ml), which was then washed with water (1×5 ml), and dried with anhydrous sodium sulfate. Following filtration to remove drying agent, the ether solvent was removed by nitrogen stream to yield the rooperol product.

EXAMPLE 3

Acetylated Rooperol

Rooperol from Example 2 (2.82 g, 0.01 mol) was dissolved in a mixture of acetic anhydride (3.06 g, 0.03 mol) and pyridine (10 ml) and stirred at 25° C. for 2–3 hours under anhydrous conditions. HPLC analysis (Example 5) of the resultant mixture afforded the HPLC chromatogram shown in FIG. 1. The structures of the compounds eluting as peaks 1, 2 and 3 were assigned as follows: peak 1 (14.35 minutes), 4,4'-diacetylrooperol; peak 2 (14.8 minutes), 3,4, 4'-triacetylrooperol; peak 3 (15.5 minutes), 3,3',4,4'-tetraacetylrooperol.

EXAMPLE 4

Inhibition of TNF-α and IL-1β Production by Rooperol

Peripheral blood mononuclear cells (PBMs) from normal human donors were separated on a Ficoll-Paque gradient and enriched in monocytes by adherence. PBMs were cultured in 12-well plates (2×10⁶ cells/ml/well) in RPMI 1640 supplemented with 5% fetal calf serum.

Cultures were stimulated with lipopolysaccharide (LPS, 20 ug/ml), with or without rooperol at concentrations of 1, 2, 5, and 10 µM, and incubated overnight in 5% $CO_2$. The cells were pelleted, resuspended in RPMI medium, and freeze-thawed five times to produce lysates. All samples were stored at –20° C. until cytokine concentrations were determined by commercial ELISA assays. The results are shown in FIG. 2.

EXAMPLE 5

Analytical HPLC

For analysis of hypoxoside, rooperoid, and rooperoid derivative-containing samples, the analytical procedure described by Kruger et al. (1993) was employed. A Hewlett Packard HP1090 M liquid chromatography system was used, equipped with a binary DR5 solvent delivery system and manual valve injector, an HP 1040 diode array detector, and an HP79994A workstation. The analytical column (4.6× 250 mm) was packed with end-capped C8-bonded silica of 5 µm regular particle size (Whatman, Maidstone, England), while a guard column (2.1×75 mm) was packed with pellicular C18-bonded silica (Whatman). An in-line extraction pre-column (2.1×30 mm) was packed with preparative grade C18-bonded silica, 40 µm particle size (Analytichem International, Harbor City, Calif.).

Operating conditions involved a linear solvent gradient programmed at a flow rate of 1.5 ml/min starting with mobile phase A (0.05M $KH_2PO_4$) to which 10% mobile phase B (acetonitrile-isopropanol, 80:20 v/v) was added after 0.01 min. This mixture was maintained for 1 minute after which a linear gradient of mobile phases A and B was begun, ending at 70% B after 16 minutes. The column temperature was maintained at 50° C.

The in-line extraction pre-column was loaded with sample (dissolved in 50 μl ethanol or in up to 200 μl of mobile phase A in the case of purified compounds; or a 200 μl aliquot of serum or urine from a human subject) and made up to 500 μl with an aqueous solution containing 8M guanidinium chloride and 1M ammonium sulfate. Blood samples were first converted to sera prior to analysis. The extraction column was flushed before and after sample introduction with 500 μl of aqueous 0.5M ammonium sulfate. The solutes trapped on the in-line extraction column were then eluted onto the analytical column by mobile phase after column switching and initiation of the analysis.

The detector was programmed to monitor the eluant at 260 nm and also to record absorption spectra from 200–400 nm.

EXAMPLE 6

Rooperol Metabolites in Serum

HPLC-purified hypoxoside (1 g) prepared as described in Example 1 was dissolved in 200 ml water and ingested orally as a single dose by an adult human volunteer. Two hours later a blood sample was collected which was subsequently analyzed for rooperol metabolites by the HPLC method of Example 5.

Chromatograms (FIG. 3) obtained with blood samples collected before (lower trace) and after (upper trace) hypoxoside administration revealed the appearance of three new peaks, designated A, B, and C, with retention times of 7.6, 8.4, and 9.6 minutes, respectively.

EXAMPLE 7

Hypoxoside Metabolites from Urine

The urine from the volunteer in Example 6 was collected over the first 24 hours following administration of hypoxoside and then processed as follows. C18-bonded silica sorbent material (200 g, 40 μm) was pre-treated with methanol and water via a column bed. Filtered urine (5 l) was passed through the sorbent bed, followed by elution in sequence with water (400 ml), aqueous methanol (10% v/v, 400 ml), aqueous methanol (30% v/v, 800 ml) and finally with methanol (400 ml) and water (400 ml). The aqueous methanol fraction (30% v/v, 800 ml) was diluted with water (1600 ml) and again passed through the sorbent bed which was then eluted with water (400 ml) and finally with methanol (400 ml). The final methanol solution was evaporated under vacuum at 50° C. to an aqueous residue which was lyophilized to yield 1 g of a mixture of hypoxoside metabolites and endogenous urine components.

A suitable volume of filtered aqueous solution of this residue (10 mg/ml) was injected onto the in-line pre-column of the analytical HPLC system (Example 5) such that 3 fractions designated A, B, and C having the same retention times as the corresponding peaks observed in serum (Example 6) were collected at the column outlet (see FIG. 4). These fractions were rendered free of mobile phase buffer salts by standard reverse phase sorption technique and lyophilized to dryness.

EXAMPLE 8

Enzyme-Hydrolysis of Urinary Metabolites

Urine metabolite fractions A, B and C were individually and selectively hydrolyzed by β-D-glucuronidase and/or arylsulfatase. D-saccharic acid 1,4-lactone (0.005 mM) and sodium sulfate (0.01M) were used to inhibit any β-glucuronidase or arylsulfatase cross-activity in the respective enzyme preparations. In each case, hydrolysis was conducted in 0.1M acetate buffer (pH 5.5) at enzyme and substrate concentrations of 1 mg/ml each incubated for 2 hours at 37° C. The products of hydrolysis were extracted into ether which was evaporated to dryness under nitrogen stream.

Comparison of the retention times of the treated compounds with that of rooperol, in light of other chemical analysis, indicated that A is rooperol 4,4'-diglucuronide, B is a mono-sulfate/mono-glucuronide derivative of rooperol, and C is rooperol 4,4'-disulfate.

EXAMPLE 9

Bioavailability of Hypoxoside/Rooperol Compounds

A. Phase I Dosing

In a Phase I dose-ranging and toxicity study, 20 human subjects were given oral doses of a hypoxoside preparation obtained by the methanol extraction procedure described in Example 1. The dosages were 1.6, 2.4, and 3.2 g. Following administration of the hypoxoside preparation, blood samples were collected periodically from the subjects for measurement of hypoxoside and its metabolites. The samples were converted to sera and processed as described in Example 5. The only hypoxoside/rooperol compounds detected were the sulfate and glucuronide metabolites of rooperol noted in Examples 6 and 7. Neither hypoxoside nor rooperol could be detected.

B. Pharmacokinetics of Hypoxoside Metabolites

In a random, multiple-dose study, 6 subjects received 800 mg of *H. rooperii* methanol-extract 3 times daily for 9 days, and blood samples were collected daily for 12 days (with the exception that no samples were collected on day 11).

For the mixed glucuronide/sulfate derivative (the major metabolite), the serum half-life was 50±16 hours. For the diglucuronide and disulfate metabolites (the minor metabolites), serum half-lives were 20±6 and 20±5 hours, respectively. The pharmacokinetic profiles of the metabolites were found to fit a single open-compartment model.

EXAMPLE 10

Oral Formulation #1

This example illustrates representative pharmaceutical formulation for oral administration, containing a rooperol derivative of the invention.

| INGREDIENTS | QUANTITY PER TABLET (MG) |
| --- | --- |
| Rooperol Compound | 400 |
| Cornstarch | 50 |
| Lactose | 145 |
| Magnesium stearate | 5 |

The above ingredients are mixed and then pressed into single scored tablets.

13

Oral Formulation #2

| INGREDIENTS | QUANTITY PER TABLET (MG) |
| --- | --- |
| Pro-drug or active compound | 200 |
| Lactose, spray dried | 148 |
| Magnesium stearate | 2 |

The above ingredients are mixed and introduced into a hard-shell gelatin capsule.

Oral Formulation #3

A liquid suspension for oral administration in accordance with the invention is as follows:

| INGREDIENTS | QUANTITY |
| --- | --- |
| Rooperol compound | 1.0 g |
| Fumaric acid | 0.5 g |
| Sodium chloride | 2.0 g |
| Methyl paraben | 0.1 g |
| Granulated sugar | 25.5 g |
| Sorbitol (70% solution) | 12.85 g |
| Veegum K* | 1.0 g |
| Flavoring | 0.035 ml |
| Colorings | 0.5 mg |
| Distilled water | 0.5 mg |

*Vanderbilt Co.

EXAMPLE 11

Topical Formulation

| INGREDIENTS | QUANTITY |
| --- | --- |
| Rooperol tetraacetate | 2.0 g |
| Polyethylene glycol 200 | 2.0 g |
| Emulsifying ointment (RP) | 8.0 g |
| Chlorocresol | 0.1%* |
| Water | 4.0 g |

While the invention has been described with reference to specific methods and embodiments, it will be appreciated that various modifications may be made without departing from the invention.

It is claimed:

1. A method of treating an inflammatory disease in a subject comprising
   administering to a subject in need of such treatment, a therapeutically effective amount of a composition consisting essentially of a substantially pure compound having the structure:

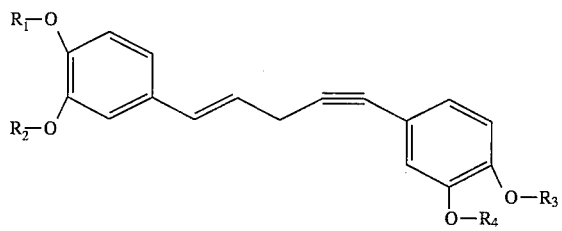

wherein $R_1$ to $R_4$ are independently selected from the group consisting of H, a lower alkylacyl group, an arylacyl group, a lower arylalkylacyl group, or a C-1-linked saccharide.

2. The method of claim 1, for treating inflammation of the large bowel, wherein $R_1$ and $R_3$ are glucose, and $R_2$ and $R_4$ are H, and said compound is administered orally.

3. The method of claim 1, for use in treating ulcerative colitis, wherein at least one of $R_1$ and $R_2$ and at least one of $R_3$ and $R_4$ are independently glucose or a lower alkylacyl group, and said compound is administered rectally.

4. The method of claim 1, for treating Crohn's disease, wherein at least one of $R_1$ and $R_2$ and at least one of $R_3$ and $R_4$ are lower alkylacyl groups, and said compound is administered orally.

5. The method of claim 4, wherein $R_1$ through $R_4$ are acetyl groups.

6. The method of claim 1, for treating respiratory inflammation, wherein $R_1$ to $R_4$ are independently selected from the group consisting of H, a lower alkylacyl group, an arylacyl group, and a lower arylalkylacyl group, and said compound is administered by inhalation.

7. The method of claim 1, for use in treating an inflammatory condition associated with the skin, wherein $R_1$ to $R_4$ are independently selected from the group consisting of H, a lower alkylacyl group, an arylacyl group, and a lower arylalkylacyl group, and said compound is administered topically.

8. The method of claim 7, wherein said condition is psoriasis.

9. The method of claim 7, wherein said condition is actinic keratosis.

10. The method of claim 7, wherein said condition is acne vulgaris.

11. The method of claim 7, wherein said condition is atopic dermatitis.

12. The method of claim 1, for use in treating eye inflammation, wherein said compound is applied or placed adjacent to the subject's eye(s).

13. The method of claim 1, for treating inflammation in the subject's peritoneal, pelvic, or pleural cavity, wherein $R_1$ to $R_4$ are independently selected from the group consisting of H, a lower alkylacyl group, an arylacyl group, and a lower arylalkylacyl group, and said administering is by injection into said cavity.

* * * * *